(12) United States Patent
Songer et al.

(10) Patent No.: US 9,345,522 B2
(45) Date of Patent: May 24, 2016

(54) BONE FIXATION SCREW AND METHOD

(71) Applicants: Matthew Songer, Marquette, MI (US);
Jason Sandstrom, Marquette, MI (US);
Francis Korhonen, Negaunee, MI (US)

(72) Inventors: Matthew Songer, Marquette, MI (US);
Jason Sandstrom, Marquette, MI (US);
Francis Korhonen, Negaunee, MI (US)

( * ) Notice: Subject to any disclaimer, the term of this patent is extended or adjusted under 35 U.S.C. 154(b) by 206 days.

(21) Appl. No.: 13/900,286

(22) Filed: May 22, 2013

(65) Prior Publication Data

US 2013/0317503 A1    Nov. 28, 2013

Related U.S. Application Data

(60) Provisional application No. 61/650,440, filed on May 22, 2012.

(51) Int. Cl.
*A61B 17/56* (2006.01)
*A61B 17/74* (2006.01)
*A61B 17/72* (2006.01)

(52) U.S. Cl.
CPC ........... *A61B 17/742* (2013.01); *A61B 17/7233* (2013.01)

(58) Field of Classification Search
CPC ........... A61B 17/7233; A61B 17/7241; A61B 17/725
USPC ..................................................... 606/62–68
See application file for complete search history.

(56) References Cited

U.S. PATENT DOCUMENTS

| | | | |
|---|---|---|---|
| 3,530,854 A * | 9/1970 | Kearney | 606/67 |
| 3,892,233 A * | 7/1975 | Vestby | 606/67 |
| 3,996,931 A * | 12/1976 | Callender, Jr. | 606/65 |
| 4,432,358 A * | 2/1984 | Fixel | 606/66 |
| 4,457,301 A | 7/1984 | Walker | |
| 4,494,535 A * | 1/1985 | Haig | 606/67 |
| 4,657,001 A * | 4/1987 | Fixel | 606/66 |
| 5,087,260 A | 2/1992 | Fixel | |
| 5,534,004 A * | 7/1996 | Santangelo | 606/68 |
| 6,261,290 B1 | 7/2001 | Friedl | |
| 6,423,066 B1 | 7/2002 | Harder et al. | |
| 8,114,078 B2 | 2/2012 | Aschmann | |
| 2002/0045900 A1* | 4/2002 | Harder et al. | 606/65 |
| 2005/0177158 A1* | 8/2005 | Doubler et al. | 606/64 |
| 2006/0084999 A1* | 4/2006 | Aschmann | 606/64 |
| 2006/0095040 A1* | 5/2006 | Schlienger et al. | 606/73 |
| 2008/0140077 A1* | 6/2008 | Kebaish | 606/64 |
| 2008/0269752 A1* | 10/2008 | Simon et al. | 606/65 |
| 2008/0269807 A1* | 10/2008 | Simon et al. | 606/290 |
| 2011/0196372 A1* | 8/2011 | Murase | 606/64 |
| 2011/0276099 A1* | 11/2011 | Champagne et al. | 606/328 |

(Continued)

*Primary Examiner* — Ellen C Hammond
*Assistant Examiner* — Stuart S Bray
(74) *Attorney, Agent, or Firm* — Device Patent LLC; Brian Janowski

(57) ABSTRACT

A screw device for compressing and fixing together a proximal and distal bone part along a surgical axis comprising: a bone screw portion comprising an elongate body inscribed with bone screw threads at a leading end of an outer surface of said body; an elongate tubular torque stabilizer portion for spanning said bone parts and comprising one or more torsion stops to engage each bone part to limit rotational movement between the bone parts and a translation stop on said torque stabilizer to seat against a portion of the proximal bone to limit translation of said torque stabilizer portion along the surgical axis; and a compressor lock portion engaging the bone screw portion and torque stabilizer portion to draw said bone screw portion proximally along the surgical axis toward said translation stop therein compressing said one parts together.

22 Claims, 14 Drawing Sheets

(56) References Cited

U.S. PATENT DOCUMENTS

2011/0282395 A1* 11/2011 Beyar et al. .................. 606/301
2012/0109127 A1* 5/2012 Overes ............................ 606/64
2012/0130370 A1* 5/2012 Kinmon .......................... 606/62
2013/0041414 A1* 2/2013 Epperly et al. ................ 606/310
2014/0371748 A1* 12/2014 Yamanaka et al. .............. 606/64
2015/0038968 A1* 2/2015 Vega et al. ...................... 606/64

* cited by examiner

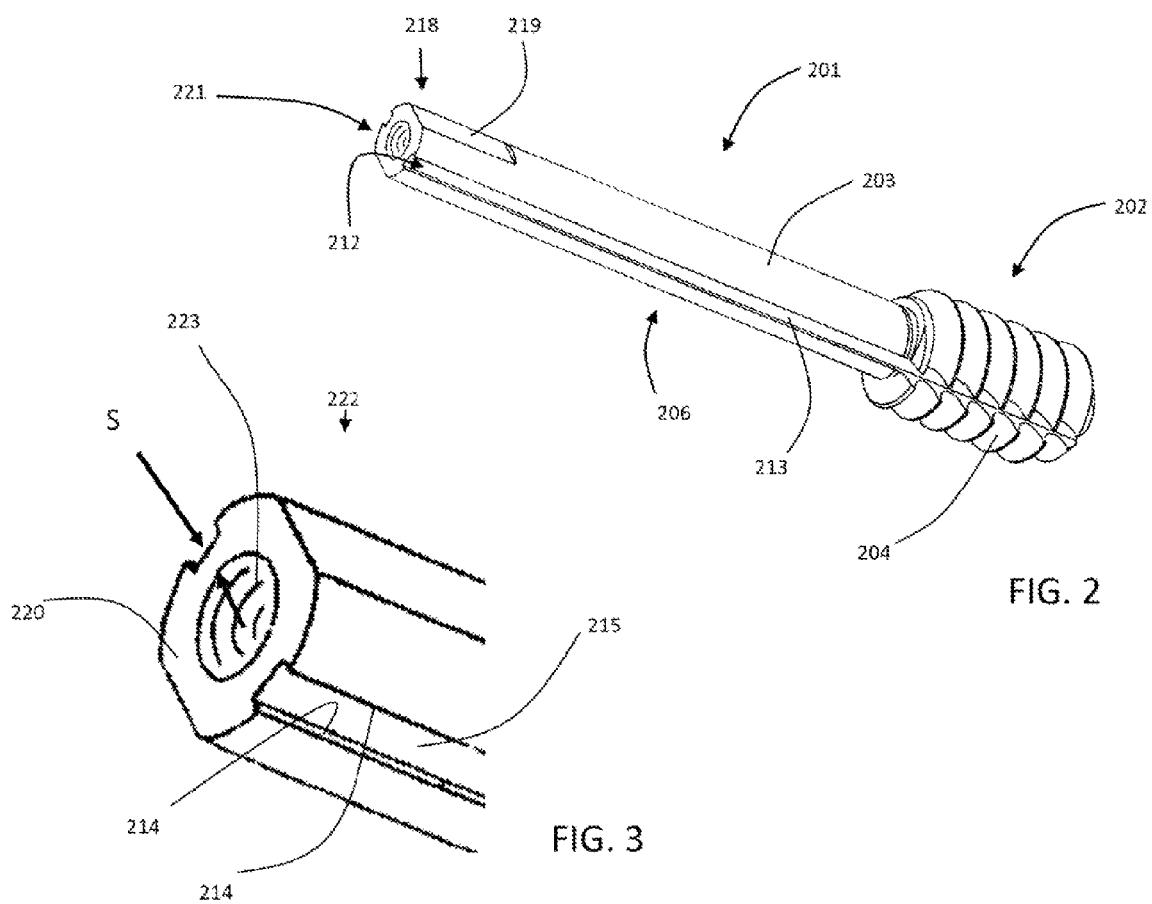

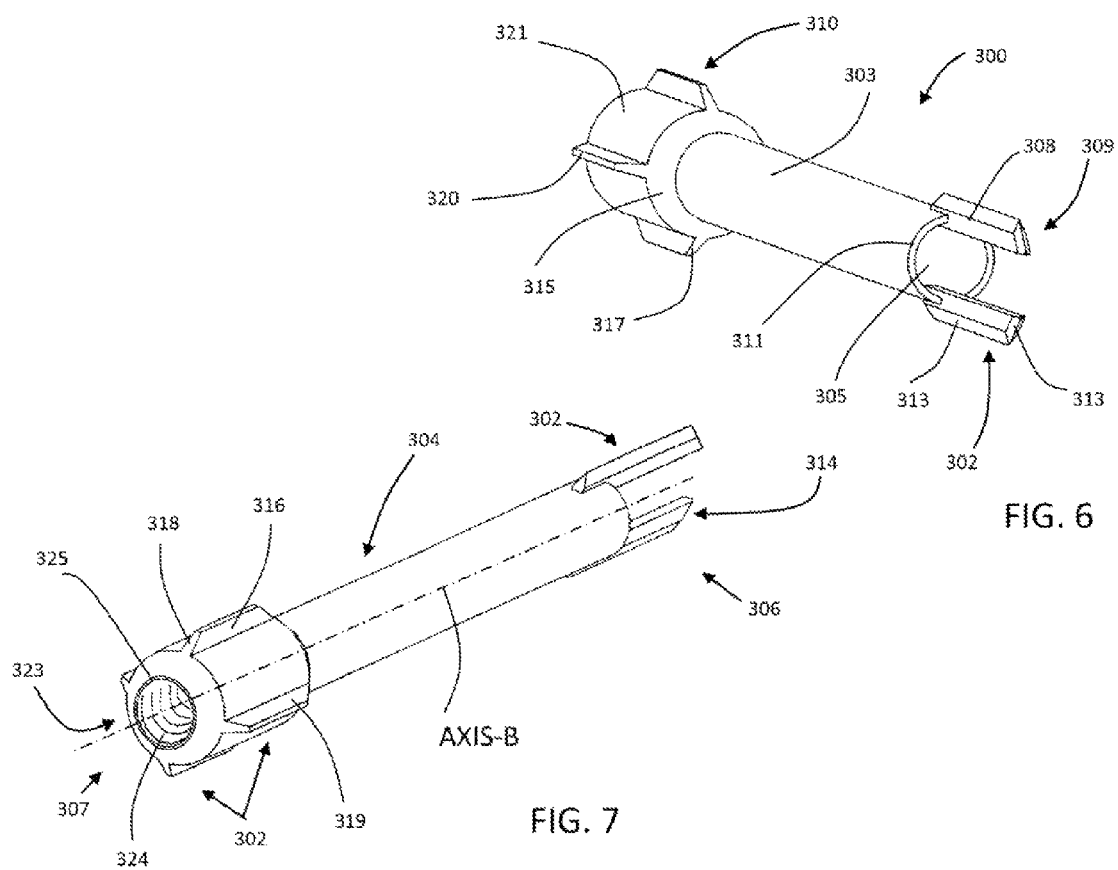

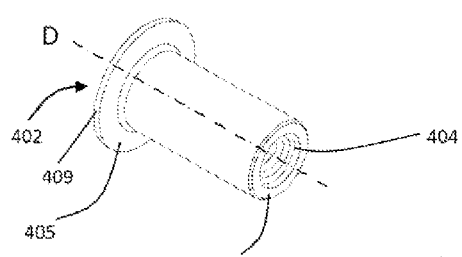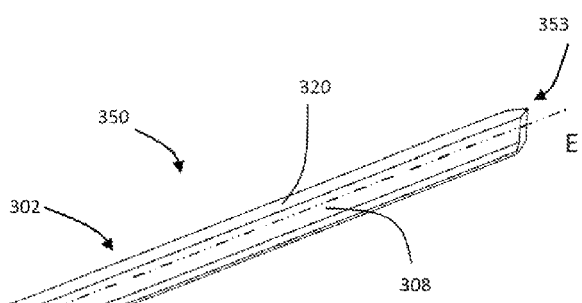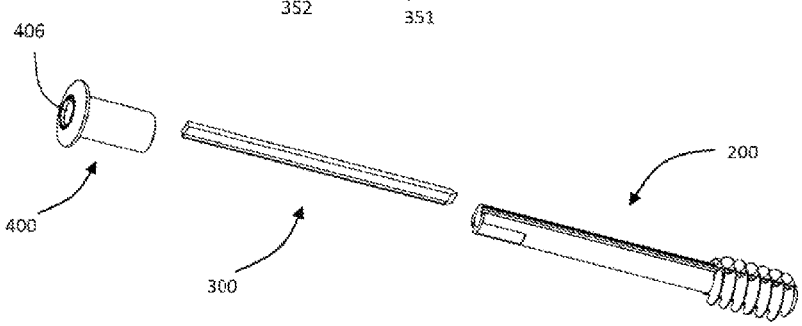

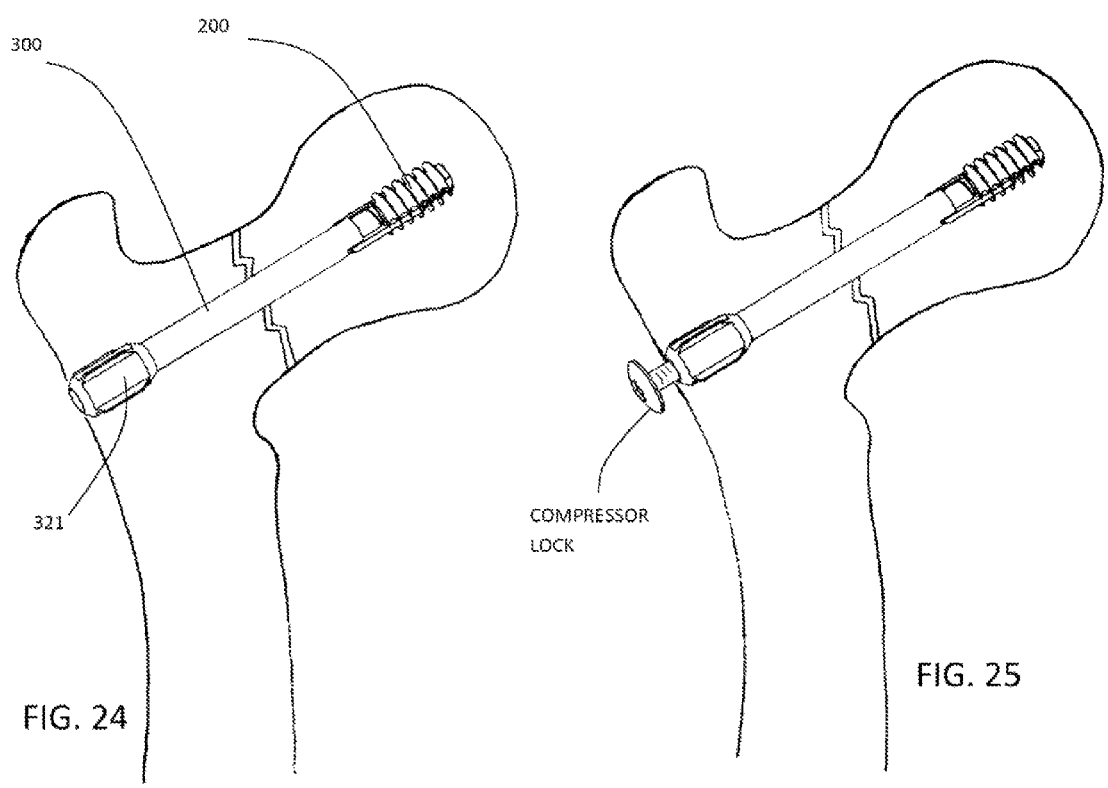

BONE FIXATION SCREW AND METHOD

The present application is a utility patent application that claims priority to U.S. Provisional Application Ser. No. 61/650,440, filed on May 22, 2012.

BACKGROUND

The present invention relates generally to the stabilization of adjacent bone portions and particularly for the stabilization of fractures. Hip fractures, for example, are a common problem that is often challenging to remedy. Femoral neck fractures of the hip typically involve the narrow neck between the shaft of the femur and the round head. The device disclosed may be used to secure and compress the bone segments on each side of the fracture site.

SUMMARY OF THE INVENTION

Disclosed herein is a bone screw assembly for stabilizing and compressing together two or more bone parts. In its preferred form this assembly is well suited for stabilizing femoral neck fractures utilizing a minimal incision at the operational site.

In one form, the invention is directed to a bone screw fixation assembly comprising a bone screw portion, a torque stabilizer portion, and a compressor lock portion. After placement of a guidewire, and boring with surgical drills, the bone screw portion comprising distally placed bone screw threads is fed over the guidewire and seated into the head of the femur at a predetermined location. A tubular torque stabilizer portion comprising a second positioner is advanced upon a first positioner on the bone screw portion therein eliminating rotational motion therebetween. Torsional stops projecting from the outer surface of the torque stabilizer portion seat into the bone therein eliminating the rotational motion between the bone and torque stabilizer and between a distal and proximal bone segment. A translation stop on an enlarged portion of the torque stabilizer abuts a portion of the proximal bone segment once the stabilizer is fully seated.

A compressor lock portion advances on the proximal end of the bone screw portion therein causing compression forces on the bone between the translation stop and the bone screw therein fixating the bone portions together and preventing torsional motion therebetween.

In one form, torsional stops on the torque stabilizer portion extend uninterrupted from a proximal to a distal end.

In one form, the torque stabilizer portion is in the form of an elongated key.

In one form, the $2^{nd}$ positioner on the torque stabilizer portion is captured within the $1^{st}$ positioner on the bone screw portion.

In one form, the torque stabilizer portion comprises an integrated fixation plate configured for fixation on a lateral surface of the femur.

In one form, the compressor lock is in the form of a screw that advances on a proximal end of the bone screw portion. In another form, the compressor lock is in the form of a cap nut that advances on a proximal end of the bone screw portion.

BRIEF DESCRIPTION OF THE DRAWINGS

FIG. 2 is a front perspective view of a bone screw portion.
FIG. 3 is a close-up view of the proximal end of the bone screw of FIG. 2.
FIG. 6 is a distal end perspective view of a preferred embodiment of a torque stabilizer portion.
FIG. 7 is a proximal end perspective view of the torque stabilizer illustrated in FIG. 6.
FIG. 12 is a front perspective exploded view of another form of a bone fixation screw assembly utilizing an elongated key form of a torque stabilizer.
FIG. 13 is a proximal perspective view of the elongated key illustrated in FIG. 12.
FIG. 14 is a distal perspective view of an alternative form of a compressor lock illustrated in FIG. 12.
FIG. 24 illustrates the torque stabilizer portion fully seated over the bone screw portion with torsional stop limiting rotation between bone segments.
FIG. 25 illustrates advancement of the compressor lock into the proximal end of the bone screw portion.

DETAILED DESCRIPTION OF THE PREFERRED EMBODIMENT

Figure 1:
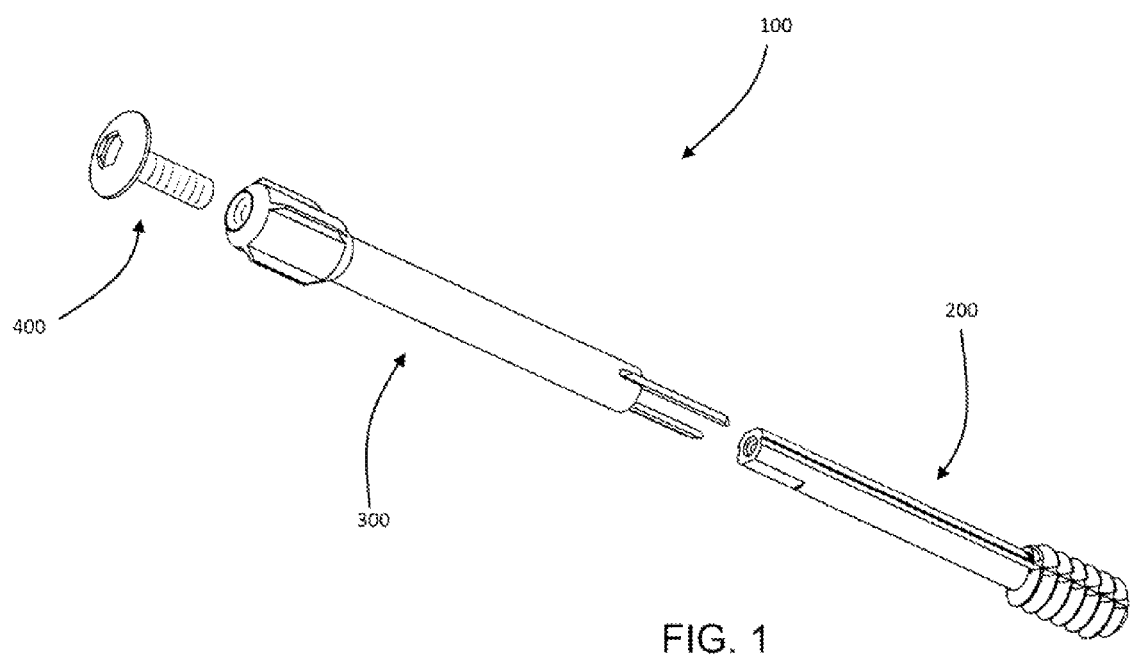
FIG. 1 is a front perspective exploded view of a preferred embodiment of a bone fixation screw assembly.
Figure 4:
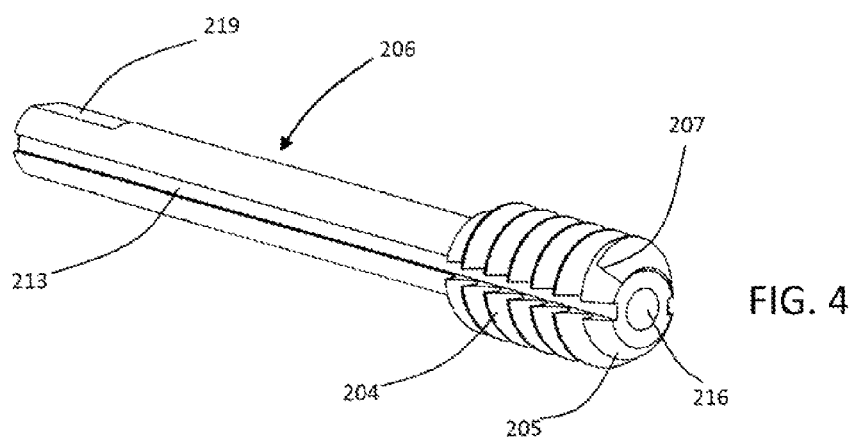
FIG. 4 is a front perspective view of the bone screw illustrated in FIG. 2 from the distal end.
Figure 5:
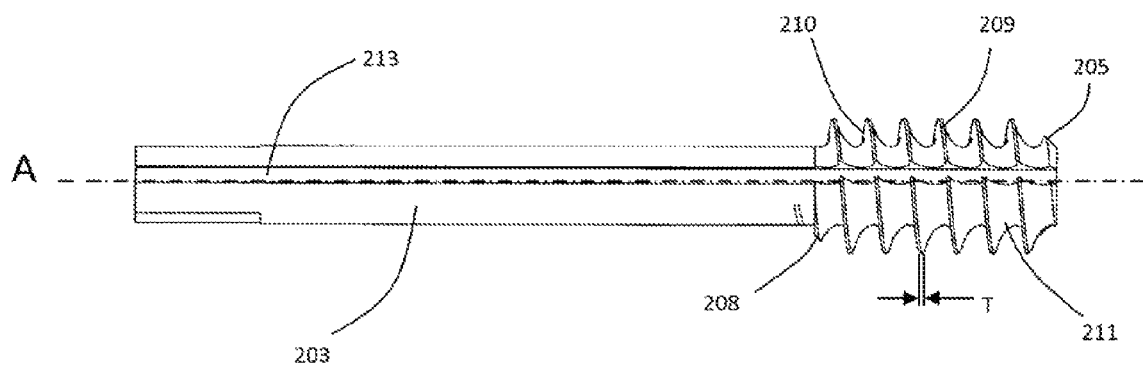
FIG. 5 is a side view of the bone screw illustrated in FIG. 2.

In a preferred embodiment illustrated in FIG. 1, the fixation screw assembly 100 comprises a bone screw portion 200, a torque stabilizer portion 300, and a compressor lock portion 400. Although not necessary, it is preferred that one or more parts of the screw assembly 100 is cannulated to pass a guide wire for guidance of the assembly to a predetermined bone site location.

In the preferred embodiment of the device, the bone screw portion 200 illustrated in FIGS. 2-5 comprises a cannulated elongate body 201 with central axis 'A'. Positioned on the distal end 202 over the outer surface 203 of the elongate body 201 are several bone screw threads 204 with a tapered lead-in 205. Proximal along the elongate body 201 from the threads 204 is a shank portion 206 of the bone screw 200 and a continuation of the elongate body outer surface 203.

The bone screw threads in this embodiment are configured to seat within the softer cortical bone of the head of the femur. For this reason, the threads may be deep and generously spaced for capture within this softer bone. For example only, the pitch may be about 8 threads per inch with a minor diameter of about 0.285 inches and a major diameter of about 0.470 inches. These values may be adjusted accordingly to accommodate the individual patient's bone density, skeletal stature, and other optimizing factors.

The bone screw portion 200 of this preferred embodiment is configured to be driven into a pre-bored hole. Although not necessary, it is preferred that the minor diameter of the screw threads 204, the diameter of the shank portion 206, and the drill diameter are of similar size. A drill diameter that is too large will reduce the torque required to seat the bone screw portion at its predetermined location, but effectively reduces the amount of screw purchase by the threads therein reducing resistance to screw pullout. A drill diameter that is too small will increase the torque required to drive and seat the bone screw portion. The screw threads may be configured with a sharp leading cutting tip 207 for self-tapping the screw into the pre-drilled hole. Alternatively, the leading thread may have a softer lead-in typically configured for a pre-tapped hole. The softer lead-in thread may also prove to be less damaging if the screw is mistakenly driven beyond the bone surface and into nearby joint space since it will be less damaging to nearby soft tissue. Similarly a soft thread lead-out 208 may ease removal of the bone screw portion for repositioning. A sharp lead-out 208 may be more effective when removal is required after osseointegration. A drill having a diameter slightly larger than the shank diameter may ease the force required to later drive the torque stabilizer portion 300 over the bone screw portion.

A variety of thread profiles may be used. The thread faces, may be adapted to improve thread purchase. For example, the leading face 209 of the threads may stand generally perpendicular to the screw axis or sloped proximal or distal. Similarly, the trailing thread face 210 may also stand generally perpendicular to the screw axis or sloped proximal or distal. The thread thickness 'T' may be adjusted for a pre-determined purchase strength, thread strength, or to produce a desired friction when driven into a pre-threaded or un-threaded hole. The threads at the major diameter may be notched (not shown). Each portion of the device including the thread surface 211 and elongate body outer surface 203 may comprise coatings such as hydroxyapatite, titanium oxides, osseospeed, osseotite, bio-tite or surface treatments such as blasting or etching to encourage osseointegration. These coatings or surface preparations can be effective at stabilizing the implant in its predetermined position. Their necessity is lessened in this embodiment since the torque stabilizing portion 300 of the assembly comprises features to not only stabilize the implant, but also stabilize position of one bone portion in relation to the other. This will be described in detail in later paragraphs.

Figure 8:
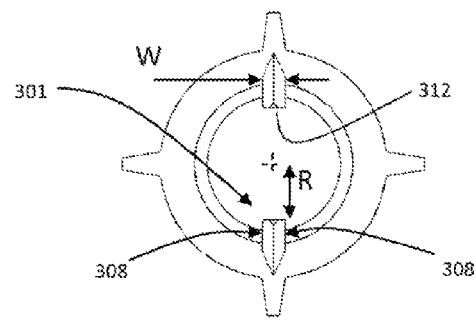
FIG. 8 is a distal end view of the torque stabilizer illustrated in FIG. 6.

The bone screw portion 200, as illustrated in FIG. 2-5, comprises a first positioner 212 and the torque stabilizer portion 300 comprises a second positioner 301 illustrated in FIG. 8. These positioners cooperate to perform several functions. In this embodiment the first positioner 212 is in the form of a linear rectangular groove 213 following the central axis 'A' and extending the entire length of the bone screw portion outer surface 203 including extending through the bone screw threads 204. Although less preferred, the first positioner 212 could stop before reaching the distal end 202 of the bone screw portion 200 or even before reaching the threads of the bone screw portion.

The first positioner 212 may take forms or profiles other than a groove 213 such as a ridge, notch, or one or more bumps. These first positioner features serve to guide the torque stabilizer portion 300 to a predetermined position over the outer surface 203 of the bone screw portion 200 elongate body 201. Alternatively, the shank portion 206 may be non-circular to serve the function of a positioner together with a complementary profiled torque stabilizer portion.

The first positioner 212 in the preferred embodiment is in the form of a groove that serves several functions. As discussed previously, this groove 213 defines a predetermined path for the torque stabilizer portion 300 to follow as it is inserted. Second, the groove 213 prevents rotation between the torque stabilizer portion 300 and the bone screw portion 200. The third function is the grooves lateral walls 214 assist in stabilizing the distal torsion stops 309, FIG. 6, as they cut through the bone therein preventing the stops 309 from breaking or bending and keeping them aligned along the cutting path for eased insertion as they cut through the bone.

Further in this embodiment, the first positioner groove 213 comprises a bottom wall 215 spaced from the inner cannula wall 216 a pre-determined distance 'S' to maximize depth of the wall 215 while maintaining sufficient strength of the elongate body 201.

The proximal end 222 of the bone screw portion 200 comprises drive surfaces 218 illustrated in this preferred embodiment in the form of opposing flat surface portions 219 inscribed into the elongate body outer surface 203. Alternatively the drive surfaces 218 could be on the proximal face 220 in the form of notches extending into the proximal face of the bone screw portion 200. As a further alternative, the drive faces 218 could be integrated with the first positioner groove 213 thus eliminating the need for a separate set of drive surfaces.

At the proximal end 222 of the bone screw portion 200 is a fastener portion 221 which may be in the form of ridges, grooves, notches, threads 223 or other feature suitable for attaching an instrument or other portions of the implant device such as a compressor lock 400. In the preferred embodiment the fastener portion 221 is in the form of threads 223 inscribed in an enlarged diameter portion of the inner cannula surface 216 of the bone screw portion 200. The fastener threads 223 extend partially down the cannulated opening but in alternative embodiments may extend to the distal end 202. The fastener threads 223 function to secure a bone screw insertion tool (not shown) to the proximal face 220 of the bone screw portion when driving and positioning the bone screw portion 200 into the predetermined position within the femoral head. As will be described later, the fastener threads 223 are later utilized by the compressor lock 400 to draw closer the bone screw portion 200 and the torque stabilizer portion 300 of the bone fixation screw assembly 100 therein compressing and thus stabilizing the fracture site.

A preferred embodiment of the torque stabilizer portion 300 of the bone reduction screw assembly 100 is illustrated in FIGS. 6-8. The torque stabilizer portion 300 comprises an elongate tube body 304 defining an inner surface wall 305 sized to slide over and enclose a non-threaded portion of elongate body outer surface 203 of the bone screw portion 200.

The outer surface 303 of the torque stabilizer 300 comprises one or more torsion stops 302 or rotation resistors to limit rotational movement about axis 'B' with respect to the surrounding bone. Two to four torsion stops at each end are preferred. The preferred embodiment comprises torsion stops 302 near the proximal end 307 and near the distal end 306. As seen in FIG. 6, a proximal torsion stop 310 is located at the proximal end of the elongate tube body 304, and a distal torsion stop 309 is located at the distal end of the elongate tube body 304 extending from the tube body outer surface 303 and leading end surface 311 of the elongate tube body 304. Illustrated in FIG. 8, these stops 309 have a width 'W' between opposing stop side walls 308 to slide with minimal friction within the first positioner groove 213. The distal torsion stop 309 also has an inner wall 312 spaced from the central axis a distance 'R'. This inner wall 312 defines the second positioner 301 that is captured within the first positioner groove 213. Distance 'R' is just enough to provide the elongate tube body 304 free movement along the bone screw portion 200.

The torsion stop 302 may be configured with cutters in the form of sharpened edges 313 at the leading end and distal radial sides furthest from the central axis 'B' of the elongate tube body. The leading and trailing edges of the torsion stops 302 may be tapered 314 to ease cutting through bone.

The torque stabilizer portion 300 comprises a distal facing translation stop 315 near the proximal end 307 of the elongate tube body 304. In this embodiment, the translation stop 315 is in the form of an enlarged portion 321 of the elongate body outer surface defining a stop surface for abutting against bone in the pre-bored hole in the bone.

Again, the proximal end 307 of the torque stabilizer portion 300 comprises one or more proximal torsion stops 310 serving to prevent rotation of the torque stabilizer portion once it is fully secured into the bone parts. In this preferred embodiment, the proximal torsion stops 310 are in the form of fins 316 extending from the enlarged portion 321 of the elongate body 304. The fins 316 comprise a lead wall 317, a trailing wall 318, side walls 319, and a distal radial wall 320. The side walls 319 may be inclined to define a sharper distal radial wall 320 edge. The leading edge 317 or trailing edge 318 of the fins 316 may be tapered and the leading edge may be sharpened to ease insertion into the bone. The leading edge surface of the torque stabilizer portion may also be sharpened for the same purpose.

Figure 9:
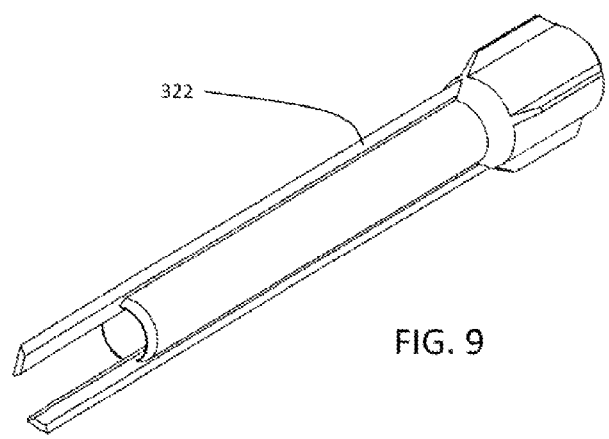
FIG. 9 is a distal perspective view of another form of a torque stabilizer comprising a continuous torsion stop.

The elongate body 304 of the torque stabilizer 300 in the operational configuration spans the bone segments. The proximal torsion stops 310 at the proximal end and the distal torsion stops 309 at the distal end of the torque stabilizer function to engage each bone part. Alternatively, the one or more continuous torsion stops 322 could be extended along the elongate body of the torque stabilizer a distance effective to span both bone segments as illustrated in FIG. 9. This modification would eliminate the need for having both proximal and distal stops 310, 309.

A fastener portion 323 illustrated here in the form of threads 324 is inscribed in the inner cannula surface 305 of the torque stabilizer portion 300 in the preferred embodiment. The fastener threads 324 extend partially down the proximal cannula opening and functions to secure a torque stabilizer insertion tool (not shown) to the proximal face 325 of the torque stabilizer portion 300 for driving and positioning the torque stabilizer portion into the predetermined position within the femoral neck and head. The proximal face 325 of the torque stabilizer portion 300 may include a taper to minimize portions of the implant from protruding above the bone surface.

Figure 10:
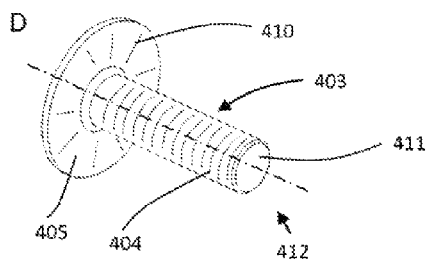
FIG. 10 is a distal end perspective view of a preferred embodiment of a compressor lock portion.
Figure 11:
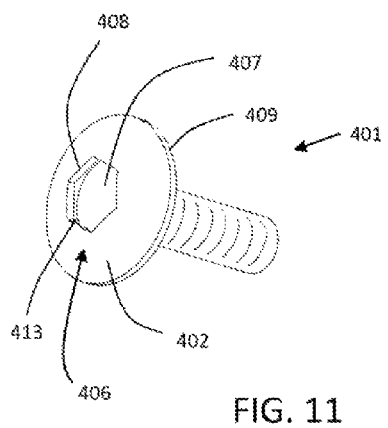
FIG. 11 is a proximal end perspective view of the compressor lock portion illustrated in FIG. 10.

The preferred embodiment of the bone fixation screw 100 assembly comprises a compressor lock 400 in the form of a screw. The screw 401 as illustrated in FIGS. 10-11 comprises a head 402 and a shaft 403. The shaft 403 includes a lead face 411, threads 404 and is configured to cooperate with the threads 223 inscribed in the inner cannula surface of the bone screw portion 200. Rotation of the screw 401 will advance the shaft 403 down the threaded cannula of the bone screw portion. Facing distal 412 on the underside of the screw is a reduction surface 405 used to abut the proximal face 325 of the torque stabilizer portion 300 therein approximating the bone screw portion 400 and torque stabilizer portions 300 together to effectively compress the fracture as the compressor lock 400 is advanced.

The compressor lock 400 comprises a drive 406, here in the form of one or more drive pockets 407 formed in the head 402 of the screw 401. The drive pocket 407 comprises 2 or more drive surfaces 408 to abut complementing drive surfaces on a screw driver tool used to transmit torque from the user to the screw. Alternatively, the drive surfaces 408 may be formed on the radial wall 409 of the screw head 402 or on an extension from the screw head. It is preferred that the head of the screw is smooth to prevent irritation to the surrounding soft tissue.

The compressor lock 400 may further comprise an antibackout feature. For example, the reduction surface 405 on the screw and the proximal surface 325 of the torque stabilizer portion 300 may be configured with interlocking splines 410 that would require overcoming the friction created between the splines before the screw can begin to back out. The lock 400 may also comprise a retainer, a feature such as an undercut groove 413 that a portion of a lock inserter may secure to prevent premature release of the lock from the instrument.

An alternative form of the device is illustrated in FIGS. 12-17. Here, one or more torque stabilizers 300 in the form of an elongated key 350 are partially captured within a first positioner groove 213 using a tongue and groove relationship. An exploded view of this assembly is illustrated in FIG. 12 and again comprises a bone screw portion 200, a torque stabilizer portion 300, and a compressor lock portion 400.

Figure 15:
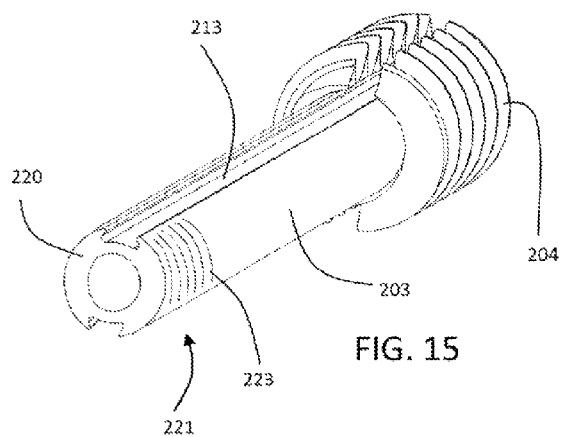
FIG. 15 is a proximal perspective view of the bone screw portion illustrated in FIG. 12.
Figure 16:
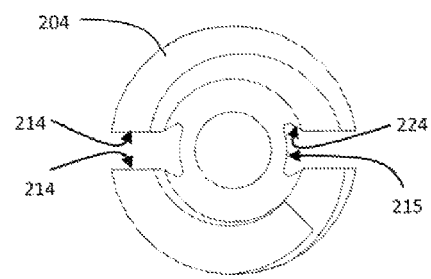
FIG. 16 is an end view of the bone screw bone screw portion illustrated in FIG. 15.

FIG. 15 illustrates the bone screw portion which again comprises a first positioner in the form of a groove 213. As illustrated in FIGS. 13 and 15, this grove 213 may be configured to position and capture the torque stabilizer 300 of FIG. 12. The groove 213 comprises a bottom wall 215, lateral wall 214, and a capture wall 224. The elongated key 350 torque stabilizer illustrated in FIG. 13 comprises a side wall 308, an inner wall 351, and a broad base wall 352 that is configured to slidingly move along axis E through the groove 213 wherein the capture wall 224 of the bone screw portion 200 holds the broad base wall 352 of the torque stabilizer within the groove. The side wall 308 of the torque stabilizer portion that extends beyond the outer surface 203 of the bone screw portion 200 into the surrounding bone is a torsion stop 302 serving to interfere with the bone to limit rotation between the bone and bone screw portion. The distal end of this torque stabilizer key 350 may comprise a cutter 353 shown here in the form of a sharpened edge. The radial wall 320 may also be sharpened to ease insertion. One or more torque stabilizer keys 350 may be used with each bone screw portion. The bone screw portion illustrated in FIG. 15 is equipped with two first positioner grooves 213 to house a torque stabilizer key 350 in each. Inscribed on the outer surface 203 near the proximal end is a fastener portion in the form of screw threads 223 which cooperate with compressor lock threads 404 (FIG. 14) during final bone fixation or threads on an insertion tool (not shown) for bone screw insertion. In this embodiment it is preferred that the threads are on the proximal outer surface 203 of the bone screw portion, however in other embodiments they could be located on the inner cannula wall as illustrated in FIG. 3 for cooperation with a compressor such as introduced in FIGS. 10 and 11.

In this embodiment (FIG. 12), the compressor lock portion is in the form of a cap nut 450 comprising internal threading 404. As with previous embodiments, the compressor lock portion comprises a reduction surface 405. Unlike prior embodiments, this reduction surface 405 is configured to drive against the adjacent cortical bone of the femur serving a similar function as the translation stop 315 described in other embodiments (FIG. 6) therein causing the bone screw portion 200 to move proximal along the surgical axis and further causing compression at the fracture site and fixation of the bone parts as the compressor lock is advanced. The compressor lock in FIG. 14 comprises a drive 406 as described in previous embodiments. The lead face 411 of the compressor reducer is configured to advance against the proximal face 325 of the torque stabilizer portion 300 therein maintaining its capture within the first positioner groove. The reduction surface 405 on the compressor lock portion may comprise anti-backout features such as splines or small teeth. In an alternative embodiment, the reduction surface 405 and the lead face 411 may be coincident.

Figure 17:
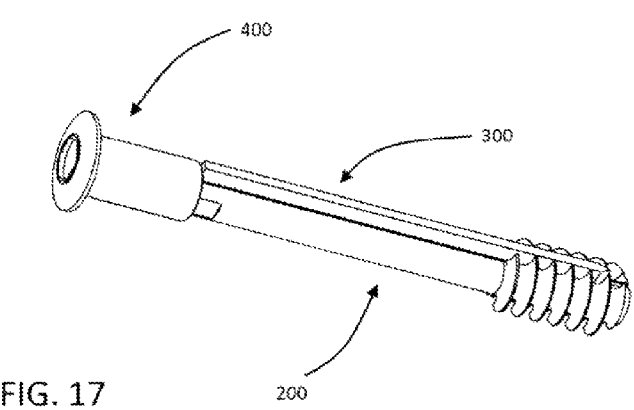
FIG. 17 is a front perspective view of the bone fixation screw assembly illustrated in FIG. 12 in its operational configuration.

This embodiment, the bone fixation screw in its operational configuration is illustrated in FIG. 17. After insertion of the bone screw portion at the surgical site, the key 350 is translated down the groove 213 cutting through the surrounding bone to cause an interference fit between the key 350 and the surrounding bone therein stabilizing the bone screw portion and the bone segments against rotation. The compressor lock (FIG. 14) is then advanced over the proximal end threads (FIG. 15) of the bone screw portion 200.

Figure 18:
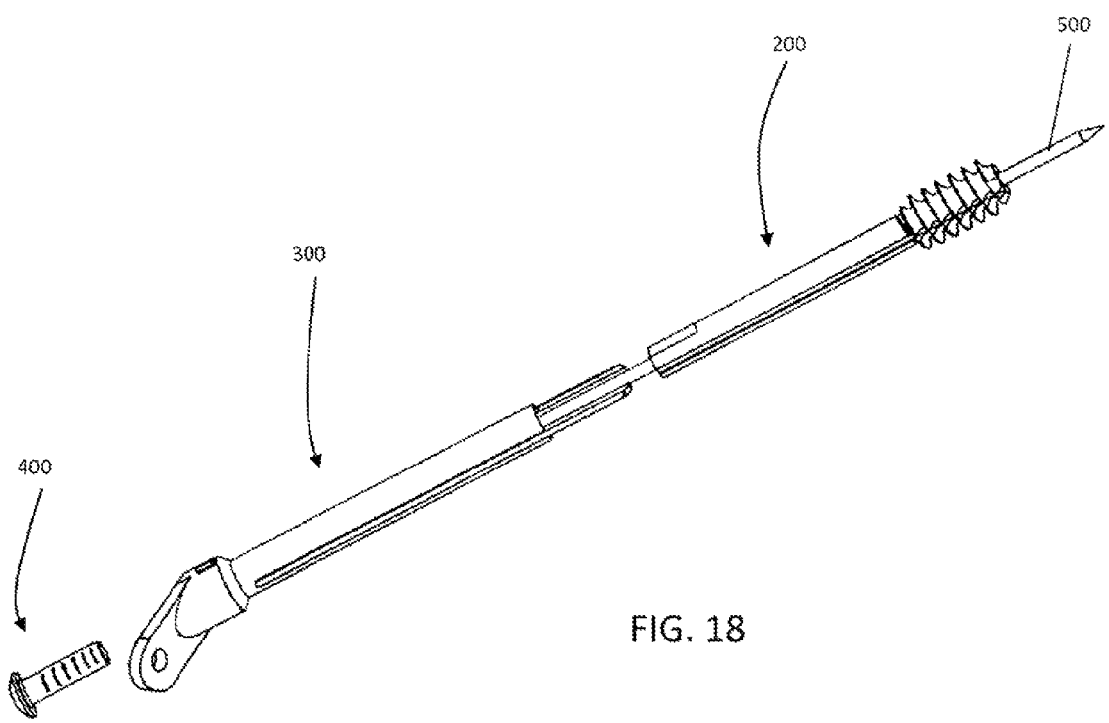
FIG. 18 is a front perspective exploded view of another form of a bone fixation screw assembly comprising an integrated fixation plate.
Figure 19:
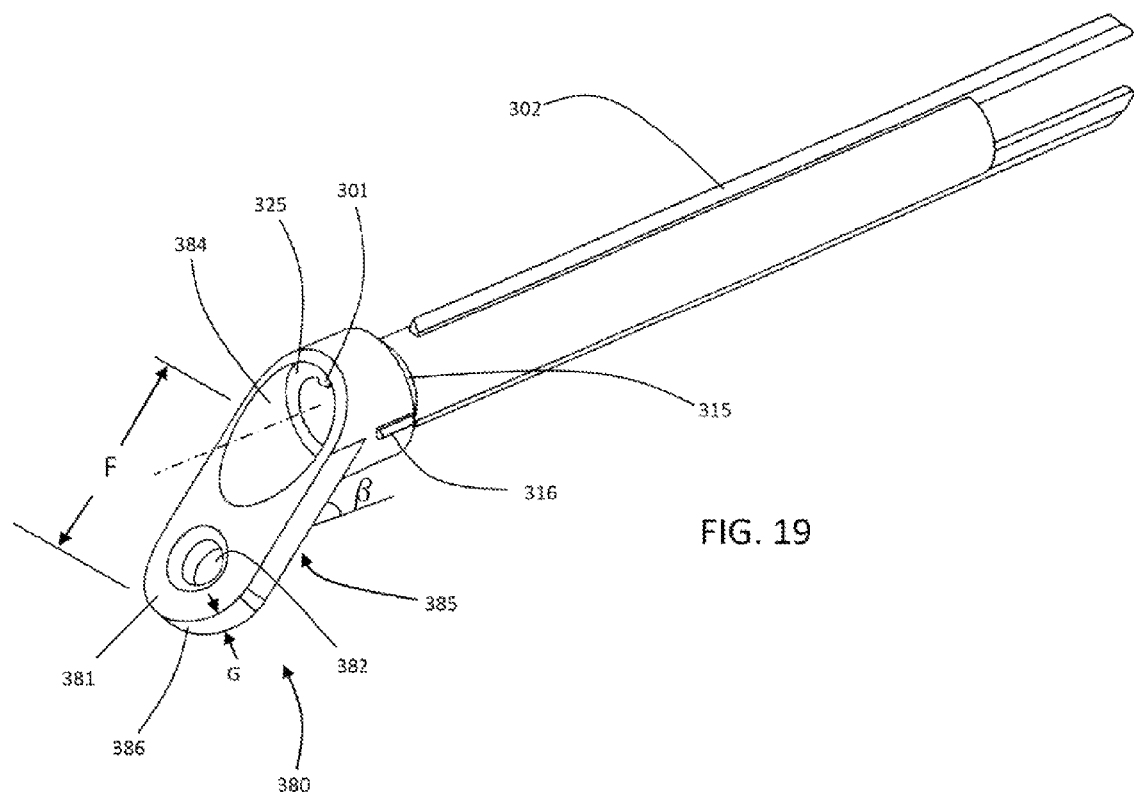
FIG. 19 is a proximal perspective view of the torsional stabilizer portion of the bone fixation screw assembly illustrated in FIG. 18.
Figure 20:
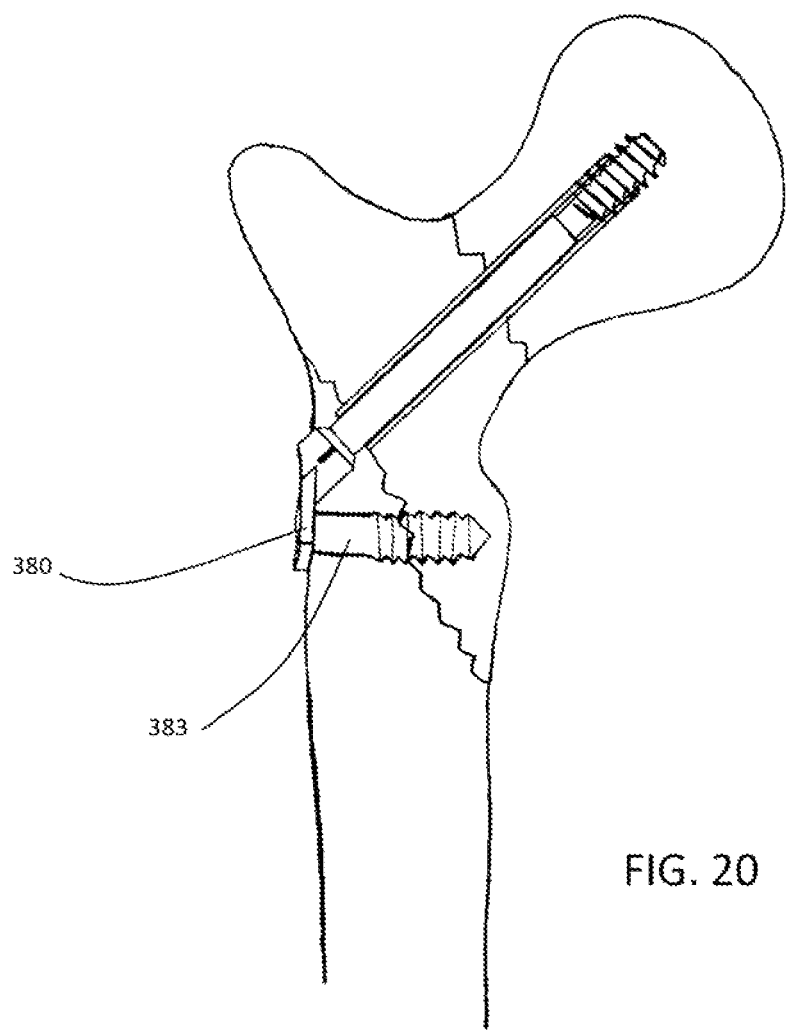
FIG. 20 is a front view illustration of the bone fixation screw assembly of FIG. 18 in its operational configuration within a fractured femur.
Figure 21:
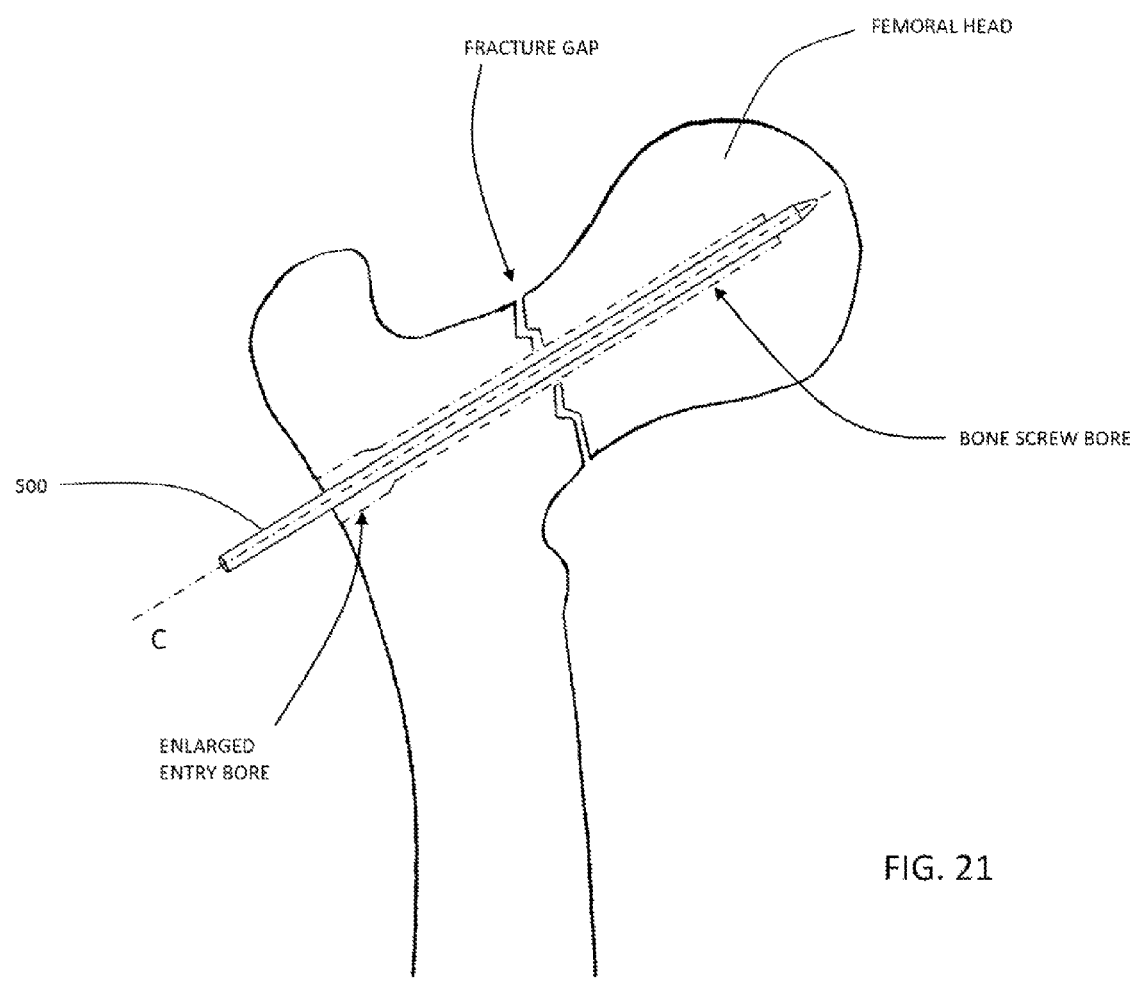
FIG. 21 illustrates placement of a guidewire within the femoral head.

Illustrated in FIGS. 18-20 is another alternative embodiment. In this embodiment the torque stabilizer 300 comprises a fixation plate portion 380 extending at a pre-determined angle 'β' from the proximal end of the torque stabilizer. The fixation plate 380 is preferably configured to span inferiorly a variable distance 'F' as required to secure the femur. Integrated in the top surface 381 of the plate 380 is one or more bone screw apertures 382 to house bone screws 383 used to fix portions of the femur against the plate. The bone screw apertures 382 may be counter-bored or counter-sunk to lower the profile of the screw within the plate. Apertures 382 may assume a round, slotted, or other profile. The fixation plate 380 secured to the femur utilizing bone screws 383 through the apertures 382 may also serve to further limit torsion and translation much like the translation stop 315 and the torsion stop 302.

The top surface 381 of the fixation plate 380 in FIG. 19 has a compression lock counter bore 384 to house the head of the compressor lock illustrated in FIG. 10-11. The bottom surface 385 of the fixation plate portion 380 may comprise a slightly concave surface profile to conform to the convex outer surface of the femur. Similarly, the top surface 381 of the plate may comprise a convex profile. The top and bottom surface of the fixation plate may define a side wall 386 with a predetermined thickness 'G' sufficient to endure the forces placed on it.

FIG. 20 illustrates this embodiment of the bone fixation screw assembly with fixation plate 380 in its operational configuration within the femur. As illustrated in the figure, the fixation plate portion 380 may be utilized to fixate an alternate fracture site within the femur. Although less preferred, the compressor lock 400 is optional in this embodiment when adequate fixation is provided by the fixation plate 380 and plate bone screws 383. In this instance the surgeon may choose to rely on natural gravitational forces to compress and stabilize the fracture. FIG. 18 illustrates an exploded view of this same embodiment (plate bone screw 383 not shown).

Cortical bone is located near the surface of the bone. When possible, it is preferred that a least a portion of the translation stop 315 and torsion stop 302 is configured to be seated within the cortical bone. For example, in FIG. 19 note that one torsional stop in the form of a fin 316 is situated at the very proximal end of the torque stabilizer to engage cortical bone.

The method of stabilizing a femoral neck fracture using the disclosed device comprises several steps generally illustrated in FIGS. 21-26. The fracture is initially evaluated using X-ray or other imaging to characterize the fracture. The surgical procedure is commonly done under a general anesthetic or a spinal block. The patient is brought to the operating room and a sterile field is created at the surgical site. If needed, tension is applied to the femur to reduce the fracture and alignment is monitored using fluoroscope.

The surgeon makes an incision at the surgical site for entry to lateral femur along surgical axis 'C'. Using imaging, a guide wire (FIG. 21) is placed down the anticipated surgical axis from the lateral femur, extending through the femoral neck and into the femoral head to a pre-determined site.

The cannula of a bone drill (not shown) is led over the proximal end of the guide wire 500. The drill is sized with a boring diameter sufficient to pass the minor diameter of the bone screw portion 200. Under power or by hand, the drill creates a bore into the femur following the surgical axis C from the lateral femur to the femoral head. The drill is removed and a second cannulated drill with a diameter similar to the diameter of the enlarged portion 321 of the torque stabilizer 300 is placed over the guide wire 500. An enlarged entry bore in the femur at a depth to house the enlarged portion of the torque stabilizer is created again by hand or power drive. Alternatively, a step-cut drill comprising a smaller first diameter at the leading end of the drill and a larger second diameter at the trailing end may be used to produce the two bores concurrently. The distal end of the enlarged bore may be flat or tapered to complement angulation of the translation stop surface 315 of the torque stabilizer portion 300. The guide wire 500 may now be removed or preferably left in position until the compressor lock 400 is installed. A tap instrument (cannulated if guide wire is present) is then advanced down the surgical path to create threads for utilization by the bone screw portion. The tap instrument (not shown) is removed. Alternatively, a bone screw portion 200 with self-tapping threads could be utilized thereby eliminating need for the tap instrument.

Figure 22:
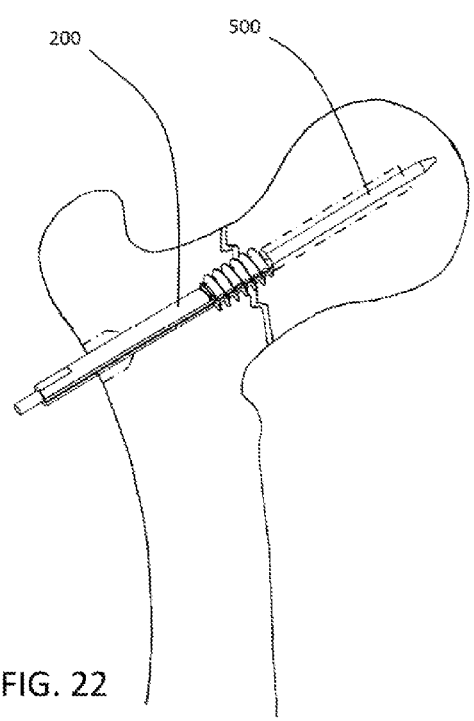
FIG. 22 illustrates the bore created by a surgical drill and advancement of the bone screw portion down the surgical path.
Figure 23:
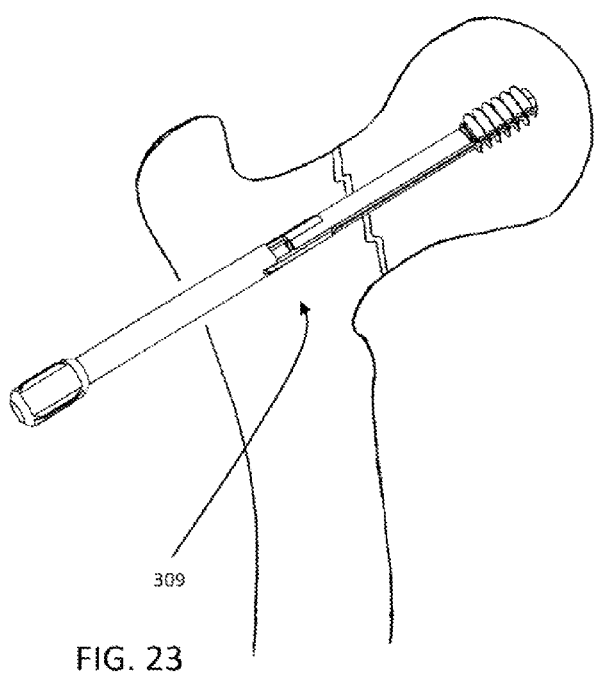
FIG. 23 illustrates the advancement of a bone screw portion to a predetermined location in the femoral head and advancement of the torque stabilizer portion through the bone so and over the shank of the bone screw portion.
Figure 26:
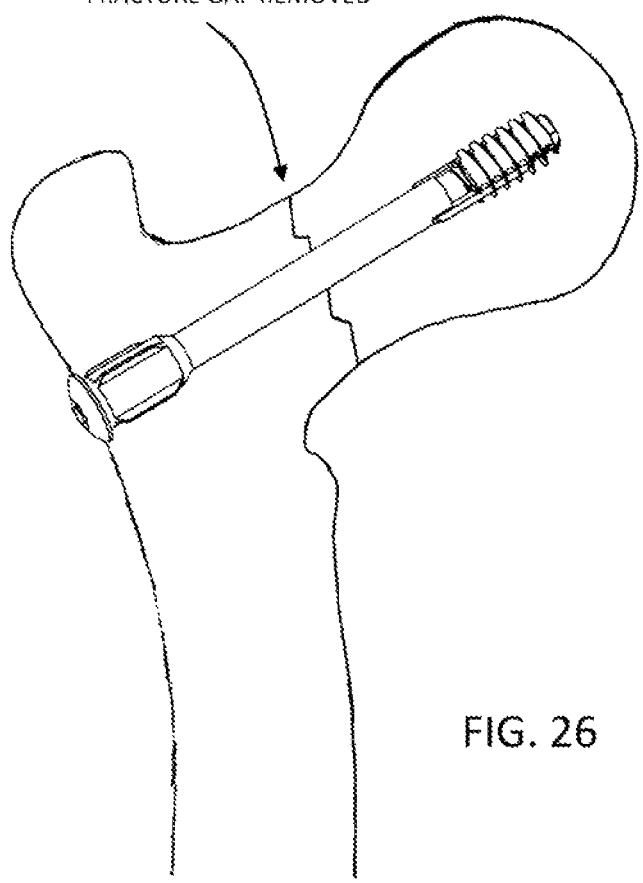
FIG. 26 illustrates a fully advanced compressor lock therein drawing the bone screw portion proximal therein closing the fracture gap.

The bone screw portion insertion tool (not shown) is attached to the fastener portion 221 of the bone screw 200. The tool is advanced causing the bone screw portion to advance down the surgical axis to the predetermined location within the femoral head (FIG. 22-23). The bone screw portion insertion tool is then removed.

A torque stabilizer insertion tool (not shown) is mounted to the torque stabilizer at the fastener portion 323 using threads 324 if so equipped. As illustrated in FIG. 23, led by the distal torsion stops 309, the torque stabilizer 300 is advanced by hand or impact on the tool along the surgical axis and positioned to capture the second positioner 301 within the first positioner groove 213. The torque stabilizer 300 continues advancement (FIG. 24) until the enlarged portion 321 of the torque stabilizer is seated within the enlarged entry bore of the femur. During final advancement, the distal torsion stops 309 and the proximal torsion stops 310 cut into the walls of the surrounding femur bone of the entry bore. Again, this step may require impacting the torque stabilizer insertion tool.

A compressor lock insertion tool (not shown) is fastened to the drive 406 of the drive pocket 407 of the compressor lock 400. The insertion tool may comprise a retainer feature to interface with the retainer feature of the compressor lock. In this embodiment the compressor lock retainer is in the form of an undercut 413 below the drive faces.

Leading with the distal end, the compressor lock's central axis 'D' is aligned with the surgical axis and rotated for advancement of the compressor lock threads into the fastener threads of the bone screw portion (FIG. 25). Once the reduction surface on the compressor lock abuts the proximal face of the torque stabilizer, the bone screw portion will be drawn toward the torque stabilizer thereby causing a reduction in fracture gaps, FIG. 26, and an increased level of compression between the bone parts thus facilitating bone fusion. As introduced earlier, anti-backout features on the compression lock will limit potential for loosening of the fixation screw assembly. Final positioning of the implant is checked with imaging.

The compressor lock insertion tool is removed and a wound closure routine can be initiated.

All portions of the assembly may be manufactured of biocompatible materials including but not limited to commercially pure titanium and titanium and stainless steel alloys. Although less preferred, portions may be manufactured from strong biocompatible polymers or ceramics.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

We claim:

1. A screw device for compressing and fixing together a proximal and distal bone part along a surgical axis comprising: a bone screw portion comprising an elongate body inscribed with bone screw threads at a leading end of an outer surface of said body; an elongate tubular torque stabilizer portion for spanning said bone parts and comprising one or more torsion stops to engage each bone part to limit rotational movement between the bone parts; said elongate tubular torque stabilizer portion enclosing a non-threaded portion of said elongate body outer surface of said bone screw portion; a translation stop on said torque stabilizer to seat against a portion of the proximal bone to limit translation of said torque stabilizer portion along the surgical axis; and a compressor lock portion engaging the bone screw portion and torque stabilizer portion to draw said bone screw portion proximally along the surgical axis toward said translation stop therein compressing said bone parts together.

2. The device of claim 1 wherein a continuous torsion stop is positioned on the torque stabilizer to span both bone parts.

3. The device of claim 1 wherein a torsion stop is positioned near the proximal end and near the distal end of the torque stabilizer.

4. The device of claim 1 wherein a portion of the torsion stop defines a second positioner for capture by a first positioner on the bone screw portion to limit rotation between the bone screw portion and the torque stabilizer portion.

5. The device of claim 1 wherein said compressor lock portion comprises a threaded shaft for engaging complementing threads near the proximal end of the bone screw portion and wherein the compressor lock portion comprises a reduction surface for engagement of a proximal face of said torque stabilizer wherein advancing said compressor lock draws said bone screw portion toward said proximal face.

6. The device of claim 1 wherein said torsion stop on torque stabilizer portion extends through a groove cut in the bone screw threads.

7. The device of claim 1 wherein the torque stabilizer portion comprises an enlarged portion near the proximal end defining a distal facing stop surface.

8. The device of claim 1 wherein the torsion stop is sharpened to cut through bone as the torque stabilizer is advanced along the surgical axis.

9. A screw device for compressing and fixing together a proximal and distal bone part along a surgical axis comprising: a bone screw portion comprising an elongate body inscribed with bone screw threads at a leading end of an outer surface of said body and a first positioner; an elongate tubular torque stabilizer portion for spanning said bone parts and comprising one or more torsion stops to engage each bone part to limit rotational movement between the bone parts; said elongate tubular torque stabilizer portion enclosing a non-threaded portion of said elongate body outer surface of said bone screw portion; a second positioner to cooperate with said first positioner on bone screw portion to limit rotation between said bone screw portion and torque stabilizer portion; and a compressor lock portion engaging the bone screw portion and torque stabilizer portion to draw said bone screw portion proximally along the surgical axis toward said translation stop therein compressing said bone parts together.

10. The device of claim 9 wherein a continuous torsion stop is positioned on the torque stabilizer to span both bone parts.

11. The device of claim 9 wherein a torsion stop is positioned near the proximal end and near the distal end of the torque stabilizer.

12. The device of claim 9 wherein a portion of the torsion stop defines a second positioner for capture by a first positioner on the bone screw portion wherein said first positioner is a groove.

13. The device of claim 9 wherein said compressor lock portion comprises a threaded shaft for engaging complementing threads near the proximal end of the bone screw portion and wherein the compressor lock portion further comprises a reduction surface for engagement of a proximal face of said torque stabilizer wherein advancing said compressor lock draws said bone screw portion toward said proximal face.

14. The device of claim 9 wherein said torsion stop on torque stabilizer portion extends through a groove cut in the bone screw threads.

15. The device of claim 9 wherein the torque stabilizer portion comprises an enlarged portion near the proximal end defining a distal facing stop surface.

16. The device of claim 9 wherein the torsion stop is sharpened to cut through bone as the torque stabilizer is advanced along the surgical axis.

17. A screw device for fixing together a proximal and distal bone part along a surgical axis comprising: a bone screw portion; said bone screw portion having an elongate body;
said elongate body having an outer surface; said outer surface of said elongate body inscribed with bone screw threads at a leading end thereof; an elongate tubular torque stabilizer portion for spanning bone parts; said elongate tubular torque stabilizer portion sized to slide over and enclose a non-threaded portion of said elongate body outer surface of said bone screw portion;
said elongate tubular torque stabilizer portion comprising at least one torsion stop to engage each bone part for limiting rotational movement therebetween; a distal torsion stop portion; a second positioner comprising an inner wall and opposing stop side walls extending from said distal torsion stop portion; wherein said inner wall is spaced from a longitudinal axis of said elongate tubular torque stabilizer portion capturing said second positioner within said first positioner groove of said bone screw portion.

18. The screw device of claim 17 wherein said elongate tubular torque stabilizer portion further comprises an enlarged head.

19. The screw device of claim 18 wherein said enlarged head is located at a proximal end of said elongate tubular torque stabilizer portion.

20. The screw device of claim 17 further comprising: a leading end surface on said elongate tubular torque stabilizer portion; said leading end surface located at a distal end of said elongate tubular torque stabilizer portion; wherein said leading end surface abuts said bone screw threads when said elongate tubular torque stabilizer portion is fully translated over said bone screw portion.

21. The screw device of claim 17 further comprising: a compressor lock portion; wherein said compressor lock portion engages said bone screw portion for drawing said bone parts together.

22. The screw device of claim 17 wherein said elongate body of said bone screw portion is cannulated for receiving a guide wire.

* * * * *